United States Patent
Acosta

(10) Patent No.: US 11,413,184 B2
(45) Date of Patent: Aug. 16, 2022

(54) FLUID COLLECTION DEVICE

(71) Applicant: Fred Acosta, Humble, TX (US)

(72) Inventor: Fred Acosta, Humble, TX (US)

(73) Assignee: ACOSTA MEDICAL GROUP, Houston, TX (US)

( * ) Notice: Subject to any disclaimer, the term of this patent is extended or adjusted under 35 U.S.C. 154(b) by 473 days.

(21) Appl. No.: 16/387,069

(22) Filed: Apr. 17, 2019

(65) Prior Publication Data

US 2019/0314189 A1  Oct. 17, 2019

Related U.S. Application Data

(60) Provisional application No. 62/770,031, filed on Nov. 20, 2018, provisional application No. 62/658,793, filed on Apr. 17, 2018.

(51) Int. Cl.
| | |
|---|---|
| *A61F 5/451* | (2006.01) |
| *A61F 5/44* | (2006.01) |
| *A61B 10/00* | (2006.01) |
| *A61B 5/145* | (2006.01) |
| *A61B 5/15* | (2006.01) |

(52) U.S. Cl.
CPC ............ *A61F 5/451* (2013.01); *A61F 5/4404* (2013.01); *A61B 5/14* (2013.01); *A61B 5/150992* (2013.01); *A61B 10/007* (2013.01); *A61B 10/0038* (2013.01)

(58) Field of Classification Search
CPC ........ A61F 5/4404; A61F 5/453; A61F 5/455; A61F 5/449; A61F 5/445; A61F 5/443; A61F 5/4405; A61F 5/4408; A61F 5/44; A61B 10/0038; A61B 5/14; A61B 5/150992; A61B 10/007; A61B 5/150366; A61B 5/150221; A61B 5/150045; A61B 10/0045; A61B 2010/008
See application file for complete search history.

(56) References Cited

U.S. PATENT DOCUMENTS

| | | | |
|---|---|---|---|
| 3,559,651 A * | 2/1971 | Moss | A61F 5/453 604/349 |
| 4,784,655 A | 11/1988 | Campion et al. | |
| 5,380,312 A * | 1/1995 | Goulter | A61F 5/453 604/352 |
| 5,423,784 A | 6/1995 | Metz | |
| 5,618,277 A | 4/1997 | Goulter | |

(Continued)

FOREIGN PATENT DOCUMENTS

| | | | | |
|---|---|---|---|---|
| EP | 0068712 A1 * | 1/1983 | ............ | A61F 5/453 |
| EP | 0068712 A1 | 1/1983 | | |

OTHER PUBLICATIONS

Int'l Search Report & Written Opinion (PCT/US2019/027901), dated Jul. 18, 2019.

*Primary Examiner* — Philip R Wiest
*Assistant Examiner* — Gregory J Feulner
(74) *Attorney, Agent, or Firm* — Hunton Andrews Kurth LLP

(57) ABSTRACT

Disclosed embodiments relate to a collection device for bodily fluids comprising a tubular material with a first end and second end. A portion of the first end is configured to be secured to a user and the tubular material may be folded over itself to form a first sheath and a second sheath. In some applications, the fluid collection devices described may be secured to a user using interlocking loops.

19 Claims, 14 Drawing Sheets

(56) References Cited

U.S. PATENT DOCUMENTS

| | | |
|---|---|---|
| 7,066,918 B2 | 6/2006 | Charles |
| 7,087,043 B2 | 8/2006 | Dolan |
| 7,658,730 B2 | 2/2010 | Conley |
| 9,101,490 B2 | 8/2015 | Mokrane |
| 9,254,218 B2 | 2/2016 | Newton, Jr. |
| 9,861,512 B2 | 1/2018 | Bourke |
| 2007/0142793 A1* | 6/2007 | Ben Youssef ........... A61F 5/455 604/329 |
| 2010/0125260 A1* | 5/2010 | White ................... A61F 13/471 604/356 |
| 2012/0130297 A1* | 5/2012 | Loescher ................ A61F 5/443 602/54 |
| 2012/0316522 A1* | 12/2012 | Carter .................... A61F 5/449 604/353 |
| 2013/0245586 A1 | 9/2013 | Jha |
| 2015/0080818 A1 | 3/2015 | Sekiyama et al. |
| 2017/0196726 A1 | 7/2017 | SanAntonio |
| 2017/0216081 A1 | 8/2017 | Acosta |

* cited by examiner

FLUID COLLECTION DEVICE

CROSS REFERENCE TO RELATED APPLICATIONS

This application is claims priority to U.S. Provisional Application No. 62/7658,793 filed Apr. 17, 2018, and U.S. Provisional Application No. 62/770,031, filed Nov. 20, 2018, the disclosures of each of which is incorporated herein by reference.

FIELD

Embodiments described herein are employed for bodily fluid collection and the protection of bodily fluid collection devices.

BACKGROUND AND SUMMARY

Traditional external catheters and bodily fluid collection devices typically utilize a sheath which can allow urine, blood, feces, or other bodily fluid to remain in contact with the user for extended periods of time. This can irritate the user's skin and, in some cases, lead to infection.

Disclosed embodiments relate to a collection device in which a single piece of tubular material is folded back on itself in order to create a first and second sheath, the second sheath outboard of the first sheath and typically extending past the open end of the first sheath. At least a portion of the first end of the tubular material is configured to be attached to the user, either directly or indirectly. The second sheath will define an interior volume in which fluid may be collected and/or directed to a subsequent collection device such as a fluid bag.

Additional disclosed embodiments relate to a bodily fluid collection device which contains multiple individually sealable pouches. These sealable pouches may be closed and separated from the remaining pouches in order to form a fluid collection bag which may be used for an extended period of time while still allowing for the removal of bodily fluids.

Still more disclosed embodiments relate to a device for the protection of an internal catheter and/or drain tube. The disclosed embodiments may be attached to the user, surrounding a drain tube in order to reduce or prevent a catheter or internal drain tube from becoming dislodged and/or becoming contaminated.

DETAILED DESCRIPTION

Figure 1:
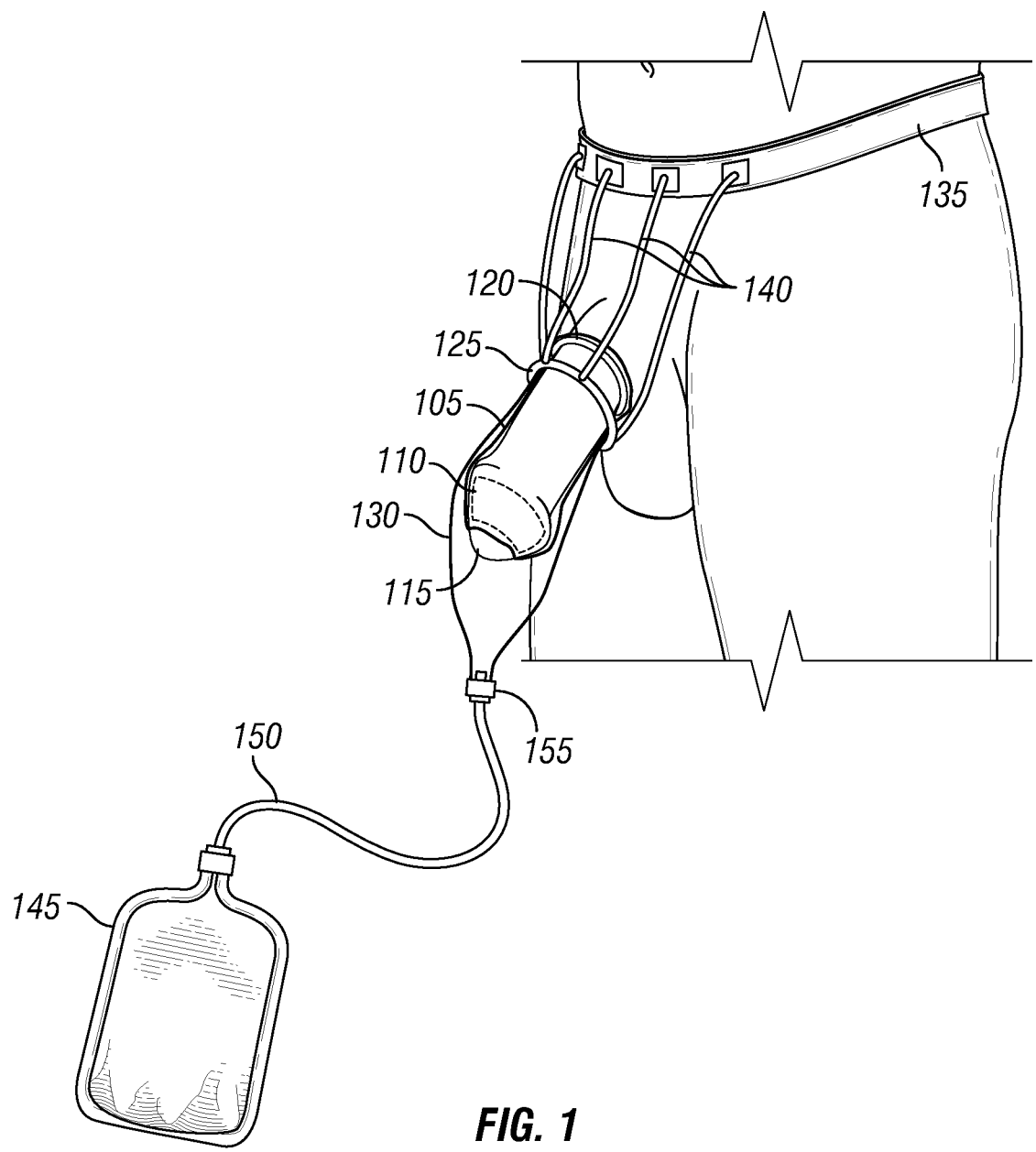
FIG. 1 depicts one embodiment of the disclosed male fluid collection device.

The following description of embodiments provides non-limiting representative examples referencing numerals to particularly describe features and teachings of different aspects of the invention. The embodiments described should be recognized as capable of implementation separately, or in combination, with other embodiments from the description of the embodiments. A person of ordinary skill in the art reviewing the description of embodiments should be able to learn and understand the different described aspects of the invention. The description of embodiments should facilitate understanding of the invention to such an extent that other implementations, not specifically covered but within the knowledge of a person of skill in the art having read the description of embodiments, would be understood to be consistent with an application of the invention Disclosed Embodiments relate to a fluid collection device. Various embodiments may be configured for use as a male urine collection device, a female urine collection device, a fecal and/or rectal collection device, and/or a device for collecting wound discharge or other bodily fluids. Alternatively or in addition to collecting bodily fluids, the disclosed embodiments may function to separate bodily fluids from the user, thereby limiting skin irritation and risk of infection. Some embodiments are designed to isolate an in-dwelling catheter, surgical drain, or other drain tube from contamination.

Disclosed embodiments utilize a tube within a tube design which creates a first sheath and a second sheath from a piece of tubular material with a first and second open end. A portion of the first side and/or the first open end may be attached to a user and the second open end may be folded back over the first portion of the tubular material to create an inner first sheath and outer second sheath. This may alternatively be described folding a portion of the first open end in-ward and attaching a portion of the first opened end to a user. Then rolling or sliding additional tubular material onto the user to create a first inner sheath and a second outer sheath.

Disclosed embodiments allow for a variety of lengths of the first sheath to be created. Various longer and shorter lengths of the first sheath allow for this design to accommodate both male and female users as well as rectal, wound care, and other embodiments. In some embodiments, the first sheath may be a substantially flat portion of the tubular material adhered to a user with little to no tubular material extending beyond the user's body. In other embodiments, a small amount of the tubular material will extend beyond the user's body. In some embodiments, the extended tubular material creates a flutter valve which allows fluid to escape but generally not return. In still other embodiments, a significant amount of tubular material will extend away from the user. In various embodiments, the first sheath may be at least about 0.5 inches long, or at least about 1 inch long, or at least about 2 inches long, or at least about 4 inches long, or at least about 6 inches long, or at least about 8 inches long, or at least about 10 inches long. In some embodiments, the first sheath may be at most about 0.5 inches long, or at most about 1 inch long, or at most about 2 inches long, or at most about 4 inches long, or at most about 6 inches long, or at most about 8 inches long, or at most about 10 inches long.

For example purposes only, the disclosed device is initially described as a male urine collection device however there are numerous alternative uses and embodiments, some of which are described herein. Elements and features described in the context of a male urine collection embodiment are not limited to such embodiments or applications and may be applied in the context of many other embodiments and applications. Other embodiments will be readily understandable and imagined by one or ordinary skill familiar with the disclosure herein.

FIG. 1 shows an exemplary embodiment of a male urine collection device. As shown in FIG. 1, a portion of the first end of the tubular material is attached to the penis. The first sheath 105 may be adhesively attached directly to the skin of the penis. In some embodiments, an intermediate layer 110, such as a hydrocolloid dressing, Tegaderm, and/or Duoderm may be directly adhered to the penis and the first sheath 105 of the tubular material may be adhered to the intermediate layer 110. This allows for a wider range of adhesives to be used to secure the first sheath 105 of the tubular material to the user while protecting the user's skin from potential irritation. Additionally, an intermediate layer 110 may facilitate removal and/or replacement of the device by protecting the user's skin from potentially painful and/or damaging forces when the adhesively secured portion of the device is removed.

If the first sheath 105 of the material is adhesively attached to the skin of the penis or an intermediate layer 110, the adhesive attachment may act as a seal which prevents urine and/or other bodily fluids from flowing between the skin of the penis and the first sheath 105. This helps to prevent potential irritation or infection of the skin. In some embodiments, the intermediate layer 110 may be shaped as a generally circular umbrella with a central opening to allow urine or other bodily fluids to pass through the opening in the intermediate layer. Preferably the first sheath 105 is attached to the glans of the penis, more preferably the material is attached less than about 0.5 cm from the meatus. In some embodiments, adhesive attachment of the first sheath may allow a user to move or be supine while still preventing significant contact between the user and any collected urine or other bodily fluids. In some embodiments, a jelly seal, hydrocolloid dressing, or other moisture barrier may be utilized between the skin of the penis and the first sheath 105 in order to create a moisture barrier, further preventing contact between urine or other bodily fluids and the user's skin. In some embodiments, the jelly seal, hydrocolloid dressing, or other moisture barrier may be attached to the intermediate layer which is attached to the penis. In some embodiments, a jelly seal may be used as an intermediate layer. In some embodiments, the jelly seal may be applied around the head of the penis, and/or along the length of the penis to prevent contact between the user's skin and bodily fluid. It will be appreciated that the disclosed jelly seal and/or intermediate layers may be used with all of the other embodiments described herein. Although the invention is primarily described in terms of a male urine collection device, all of the disclosed features may be applied to the other embodiments as well.

In some embodiments, the first opening 115 of the first sheath 105 may be adhered to the penis such that a portion of the penis extends through the first opening 115 of the first sheath 105 as shown in FIG. 1. In other embodiments, the first sheath is secured to the penis such that a portion of the first sheath extends beyond the glans of the penis. In such embodiments the tubular material which extends beyond the glans of the penis may be configured to serve as a check valve or flutter valve which allows fluid to easily exit the first sheath but generally prevents fluid from entering the first sheath.

FIG. 1 shows an exemplary embodiment of the disclosed male urine collection device. As shown in FIG. 1, the first sheath 105 may be positioned on the user's penis with a first opening 115 adhesively secured around the meatus. The first sheath 105 is secured in place using a first retaining loop 120 and second retaining loop 125. The second sheath 130 may be folded over the first retaining loop 120. The inner diameter of the second retaining loop 125 is less than the outer diameter of the inner retaining loop and the second retaining loop may be attached to a harness 135 using a strap 140. The second sheath 130 may extend past the first sheath 125 and be connected to a collection bag 145. In some embodiments, the second sheath 130 may be attached to a drain tube 150 using a one-way valve 155.

Figure 2:
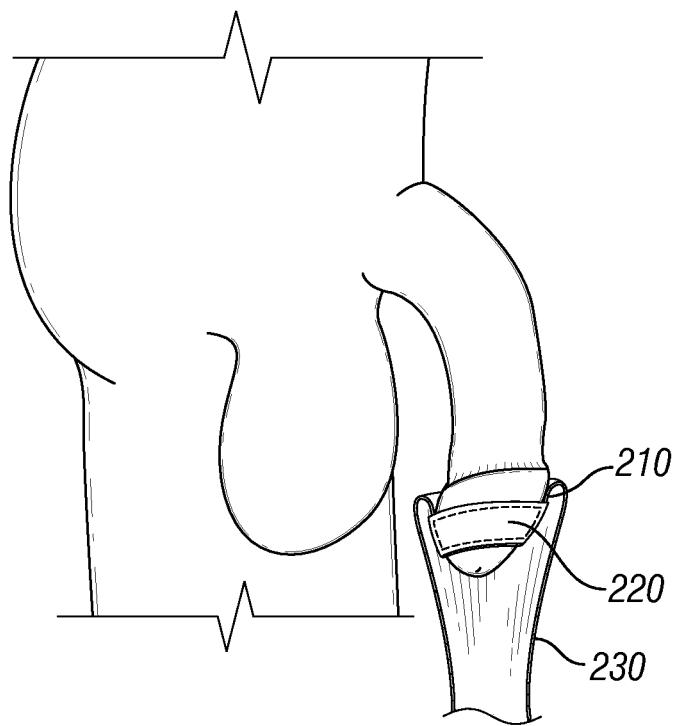
FIG. 2 shows one embodiment of the disclosed male fluid collection device during installation.

FIG. 2 shows an exemplary embodiment of the disclosed device as it is being installed. As shown in FIG. 2, the first sheath 210 of the tubular material may be secured to the user using an adhesive 220. The remaining material of the tubular material may be folded over the first sheath 210 to form the second sheath 230.

Figure 3:
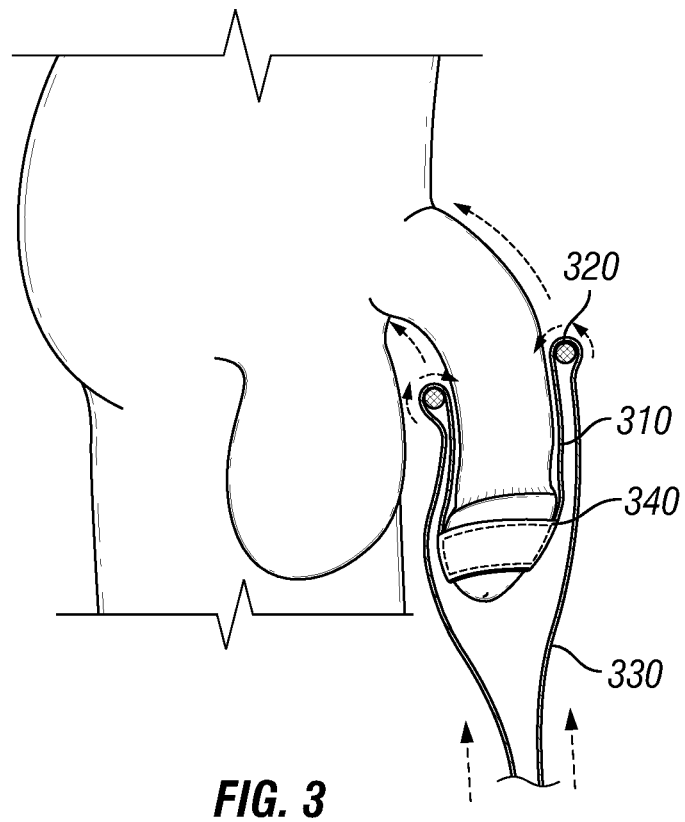
FIG. 3 shows one embodiment of the disclosed male fluid collection device during installation.

FIG. 3 shows an exemplary embodiment of the disclosed device being installed. As shown in FIG. 3, when the first sheath 310 is secured to the user, a first retaining 320 loop may be slid over the penis, outboard of the first sheath 310. The first sheath 310 may be secured to an intermediate layer 340 which is, itself, secured to the user. When the remaining tubular material is folded over the first sheath 310, the second sheath 330 will be outboard of the first retaining loop 320 and the first sheath 310.

The first loop has an inner and outer diameter and is used to maintain the device in position on the user. The inner diameter of the retaining loop is smaller than the outer diameter. The first retaining loop may be a substantially circular ring but may be any other shape as well including but not limited to squares, rectangles, triangles, and irregular shapes. The term "diameter" is not intended to limit the retaining loop to circular or elliptical configurations. In certain embodiments, the loop is generally sized to fit around a penis but many different sizes and configurations may be used depending on the conditions and circumstances. In some embodiments, the inner diameter may be at least about ½ of an inch, at least about 1 inch, at least about 2 inches, at least about 4 inches, at least about 6 inches, or larger. In some embodiments, the inner diameter may be at most about ½ of an inch, at most about 1 inch, at most about 2 inches, at most about 4 inches, at most about 6 inches, or smaller. In some embodiments, the first retaining loop 320 is configured to avoid compressing the penis. This may avoid potential complications associated with reduced blood flow to the user's penis.

In certain embodiments, the retaining loop may be at least about ⅛ of an inch thick, at least about ¼ of an inch thick, at least about ½ of an inch thick, at least about 1 inch thick, at least about 1½ inches thick, at least about 2 inches thick or thicker. In some embodiments, the retaining loop may be at most about ⅛ of an inch thick, at most about ¼ of an inch thick, at most about ½ of an inch thick, at most about 1 inch thick, at most about 11 inches thick, at most about 2 inches thick or thinner. The outer diameter will vary depending on the inner diameter and the general thickness of the retaining loop.

Figure 4:
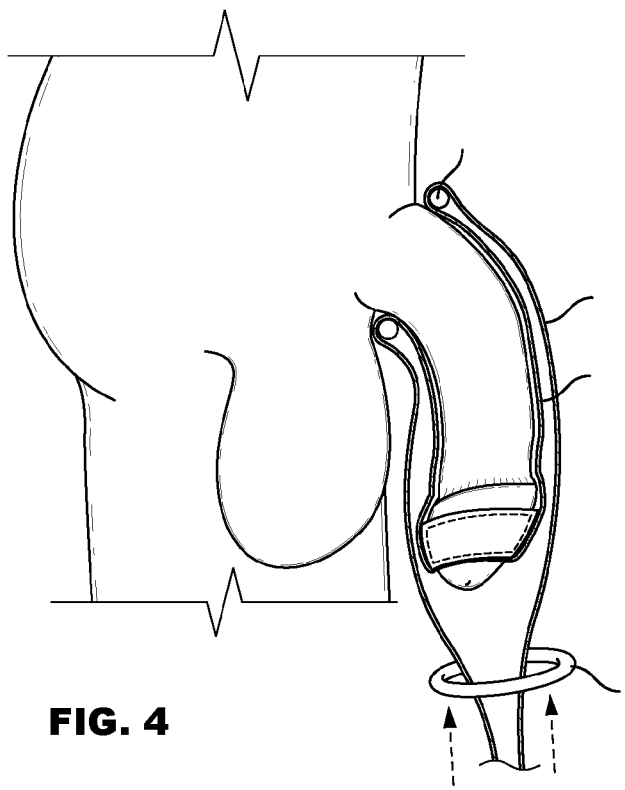
FIG. 4 shows one embodiment of the disclosed male fluid collection device during installation.

FIG. 4 shows the installation of an example embodiment. As shown in FIG. 4, The second end of the tubular material may be folded over onto itself, creating a second sheath 410 outboard of the first sheath 420 and outboard of the first retaining loop 430. The second sheath 410, once created, defines an interior volume which contains, in this embodiment, the first retaining loop 430, the first sheath 420, and the penis of the user. The second sheath 410 may be configured to extend beyond the opening in the first sheath 420 and beyond the glans of the penis. A second retaining loop 440 may be slide over the second sheath 410 and engage with the first retaining loop 430. Due to the tubular material being folded over on itself, the interior volume defined by the second sheath 410 is sealed except for the first opening in the first sheath 420 and the second opening in the second sheath 410. This arrangement prevents urine or any other fluid from leaking out of the device except through the opening in the second sheath 410, which is typically connected to a drain tube. Additionally, when the first opening in the first sheath 420 is adhered to the tip of the penis, urine is separated from the rest of the penis, leaving very little of the user's skin exposed to urine or other bodily fluids. In some embodiments, the second opening may be selectively attachable and/or detachable to or from a drain tube using a coupler, strap, elastic, or adhesive tape.

Figure 5:
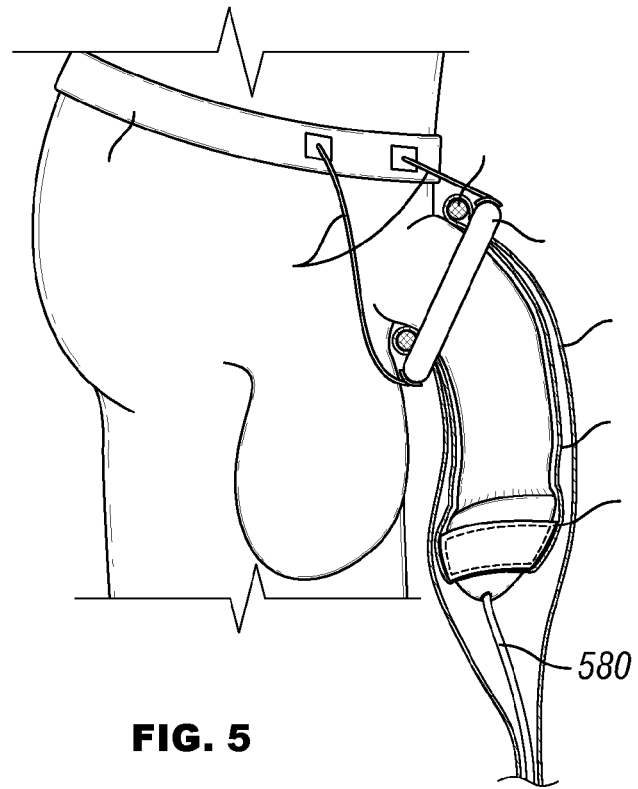
FIG. 5 shows an exemplary embodiment of the disclosed male fluid collection device.

FIG. 5 shows an exemplary embodiment of the disclosed male urine collection device. As shown in FIG. 5, A second retaining loop 510 may be positioned outboard of the second sheath 520. The second retaining loop 510 has an inner and outer diameter. The inner diameter of the second loop 510 is smaller than the outer diameter of the first loop 530 in at least one dimension. Due to the relative sizes of the first and second retaining loops, the first loop 530 will not easily pass through the second retaining loop 510. In some embodiments, the second retaining loop 510 is configured to attach to a harness 540 or other device for attaching the second loop 510 to the user. The belt and/or harness 540 used to secure the second retaining loop 510 to the user may be elastic or inelastic. The second retaining loop 510 may include attachment points for connecting a belt or harness. The second retaining loop 510 may be positioned outboard of the second sheath 520. The first retaining loop 530 may be positioned between the first sheath 550 and second sheath 520 and closer to the body of the user than the second retaining loop 510. In this arrangement, as shown in FIG. 5, the first retaining loop 530 will be held in place between the body of the user and the second retaining loop 510 as, due to their relative sizes, the first retaining loop 530 cannot easily pass through the second retaining loop 510. The second retaining loop 510 may be secured to the user using a harness 540 and a strap 560. The belt or harness 540 securing the second retaining loop 510 may be configured to avoid excessively compressing the patient and/or may be configured to allow the patient to move freely without displacing the second retaining loop 510.

As shown in FIG. 5, in some embodiments, the first sheath 550 may be secured to the user using an intermediate layer 570. An in-dwelling catheter, such as, for example, a Foley catheter, or the drain tube for an in-dwelling catheter 580 may exit the user's urethra and pass through the opening in the first sheath 550 into the volume defined within the second sheath 520. In such embodiments, the in-dwelling catheter 580 is substantially isolated from the outside environment, thereby reducing the risk of infection as the catheter site.

In one non-limiting example, if a user has been fitted with an internal catheter, such as, for example, a Foley catheter, in some embodiments, the first opening of a first sheath may be adhesively attached to the glans of a user's penis.

The tubular material of an exemplary embodiment may be folded over upon itself, forming a second sheath as described herein. The drain tube of the catheter may exit the user's penis into the volume defined within the second sheath. The second opening in the second sheath may be selectively sealed around a lower portion of the catheter drain tube. In this exemplary arrangement, the point at which the Foley drain tube exits the user's body is contained within a sealed space defined by the second sheath. The device may be secured to the user using first and second retaining loops as described. This allows embodiments of the disclosed fluid collection device to be held in position without impacting the use of the internal catheter and simultaneously reducing the risk of contamination or infection. It will be appreciated that some drain tube protection embodiments may be equally useful for the protection of female internal catheters, surgical drains, and other situations in which a drain tube exits a user's body.

Figure 6:
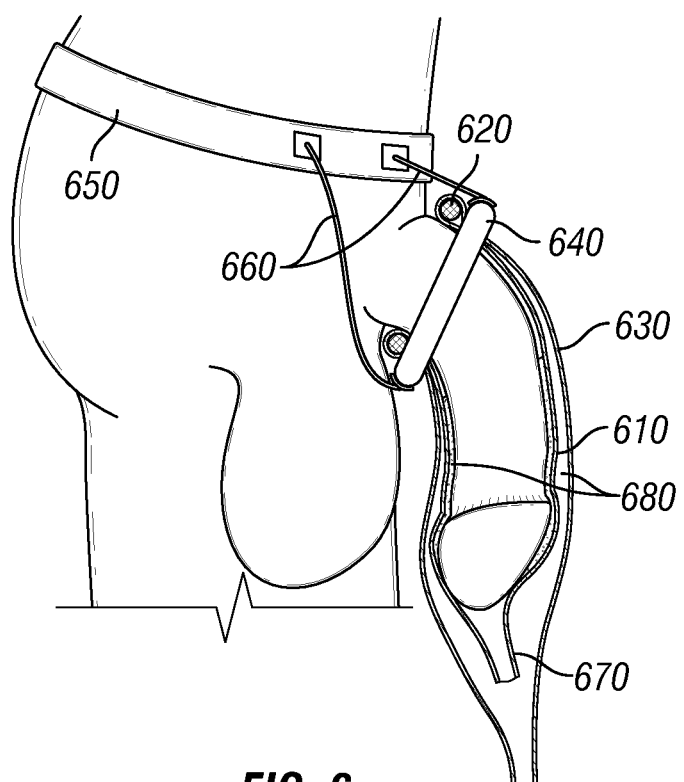
FIG. 6 shows an exemplary embodiment of the disclosed male fluid collection device.

FIG. 6 shows an exemplary embodiment of the disclosed male urine collection device utilizing a flutter valve. The exemplary embodiment of FIG. 6 shows a first sheath 610, first retaining loop 620, second sheath 630, and second retaining loop 640. The second retaining loop 640 is attached to a harness 650 using a strap 660. The first sheath 610 extends beyond the glans of the penis and terminates in a flutter valve 670. The flutter valve 670 allows urine from the user to exit the space on the interior of the first sheath 610 and prevents urine from re-entering the space on the interior of the first sheath 610. This arrangement may allow urine to exit the user and flow into the volume defined within the second sheath 630, thereby preventing the urine or other fluid from significantly contacting the user's skin. In some embodiments, a jelly seal 680 may be applied within the interior of the first sheath 610 between the user's skin and the first sheath. The jelly seal 680 may prevent any fluid from migrating along the interior of the first sheath, thereby further isolating the user's skin from contact with urine or another fluid. A jelly seal 680 may also be applied between the first and second sheaths in some embodiments in order to promote the flow of urine away from the user.

In some embodiments, one end of a strap or a harness may be attached to the second retaining loop and the other end may be adhesively secured to another area of the user's body either directly, or with an intermediate layer such as a hydrocolloid dressing. In certain embodiments, a strap may be adhesively secured to the user's leg, thigh, hip, and/or buttocks. In some embodiments, the straps and/or harness are connected to the user without adhesives. These arrangements allows the fluid collection device to be held in place without requiring the device to be adhered to the pelvis of the user, and/or without requiring the user to shave.

Many embodiments strive to minimize the amount of user's skin that is substantially isolated from circulating airflow. This may be done by utilizing retaining loops that are entirely made of a mesh or mesh-like material or utilizing retaining loops that are enclosed in a mesh material, thereby allowing airflow between a retaining loop and the user's skin. In some preferred embodiments, retaining loops will be constructed of a flexible or elastic material for improved comfort. Retaining loops may be made of material including, but not limited to, metal, polymers, rubber, silicone, cloth, fabric, mesh materials, and combinations thereof.

The second opening of the second sheath is typically connected to a drain tube. This allows fluid to be removed from the volume defined by the second sheath and transferred to a collection bag. In some embodiments, the second opening is selectively attachable or detachable to the drain tube, thereby allowing the drain tube to be replaced without removing the fluid collection device. This selective attachment may be realized using couplers, straps, elastic materials, and/or adhesives.

In some embodiments, adhering a portion of the first end of the tubular material to the penis, directly or indirectly using intermediate layers, and utilizing the disclosed first and second retaining loops to secure the device allows the disclosed male urine collection device to be used without compressing or without substantially compressing the penis.

Some disclosed embodiments may be used as an external female urine collection device. Such embodiments generally function in a similar manner as the male embodiments described herein with certain modifications which will be appreciated by one of ordinary skill.

Figure 7:
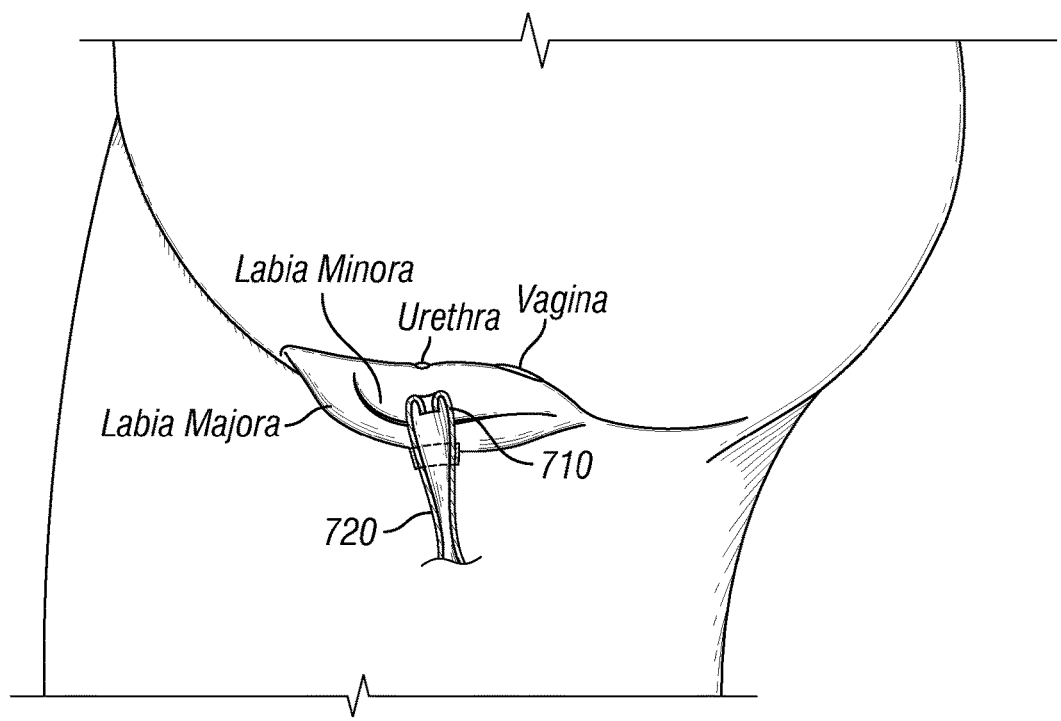
FIG. 7 shows an exemplary embodiment of the disclosed female fluid collection device during installation.

FIG. 7 shows an exemplary embodiment of a female urine collection device with a first sheath 710 which may be adhered or otherwise attached to the user around the user's urethra. The tubular material may be folded over the first sheath to form the second sheath 720.

Figure 8:
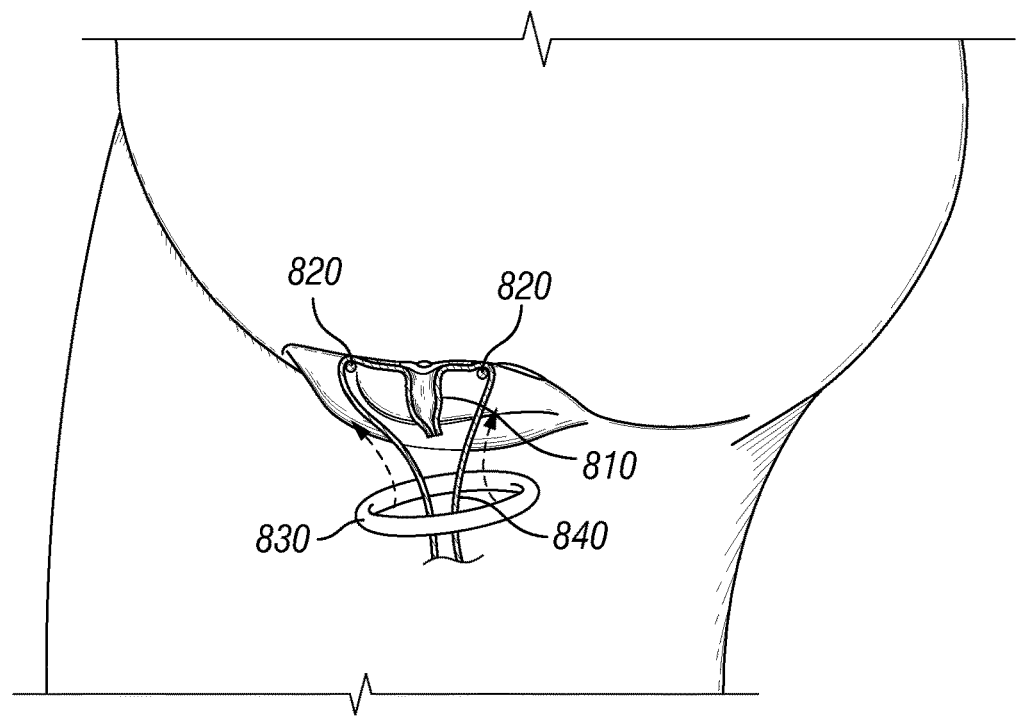
FIG. 8 shows one embodiment of the disclosed female fluid collection device during installation.

FIG. 8 shows an exemplary embodiment of a female urine collection device being installed. As shown in FIG. 8, a portion of the first sheath 810 of the tubular material may be adhered to the labia, rather than the penis, such that the first opening in the first sheath 810 substantially surrounds the user's urethra. In some embodiments, the first opening of the first sheath 810 may be adhered to the labia such that the first opening is substantially surrounding the urethra, leaving very little if any of the tubular material of the first sheath 810 extending away from the user. In other embodiments, the sheath 810 is secured to the labia such that the a portion of the first sheath 810 extends outward, creating more of a first sheath which may function as a flutter valve.

The tubular material may be adhesively secured to the labia majora, labia minora, and/or other part of the user's body. In preferred embodiments, the tubular material is secured to the labia majora less than about 0.5 cm from the labia minora. In many embodiment, the adhesively secured material creates a seal preventing urine or other bodily fluids from contacting much of the user's skin.

As shown in FIG. 8, a first retaining loop 820 may be positioned substantially surrounding the opening of the urethra, thereby retaining the first sheath 810 which may be adhered to the user. A second retaining loop 830 may be positioned outboard of the second sheath 840 and positioned to engage the first retaining loop 820 in a substantially similar manner as described in the context of a male urine collection device. The inner diameter of the second retaining loop 830 is less than the outer diameter of the first retaining loop 820.

Figure 9:
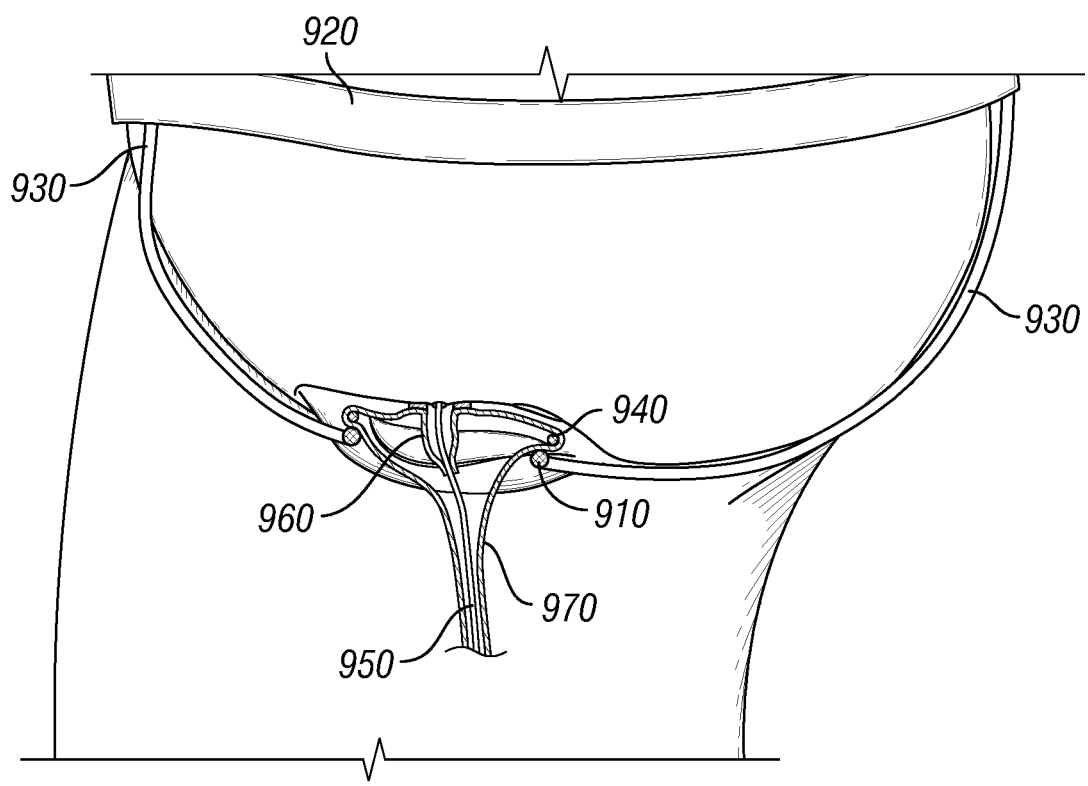
FIG. 9 shows an exemplary embodiment of the disclosed female fluid collection device.

FIG. 9 shows an exemplary embodiment of a female urine collection device. As shown in FIG. 9, a second retaining loop 910 may be secured to the user using a harness 920 and straps 930. An ordinary artisan will appreciate that in order to retain the collection device in place, an elastic belt or harness 920 may be utilized with female users as the first retaining loop 940 and second retaining loop 940 will not be additionally held in position by the user's penis. Retaining loops may be oval and/or contoured in any shape to better accommodate the female anatomy. In some embodiments, the first retaining loop 940 will be oval and contoured in shape and the second retaining loop 910 may be substantially any suitable shape capable of retaining the first retaining loop 940 in place as previously described. It will be appreciated that in some embodiments, the first and/or second retaining loops may not be circular. Nonetheless, the term "diameter" is intended to cover a cross-sectional distance from a point on one side of a shape to a point on the other, substantially opposite, side and is not intended to limit retaining loops to circular or round shapes.

As shown in FIG. 9, the disclosed female urine collection device maybe used with an in-dwelling catheter 950. A drain tube of the in-welling catheter 950 may pass through the first sheath 960 and second sheath 970, thereby isolating the catheter from the outside environment and reducing the risk of infection.

It will be appreciated that other bodily fluids besides urine may be collected by the disclosed embodiments. In particular menstrual blood or vaginal discharge may be collected with some disclosed embodiments.

Figure 10:
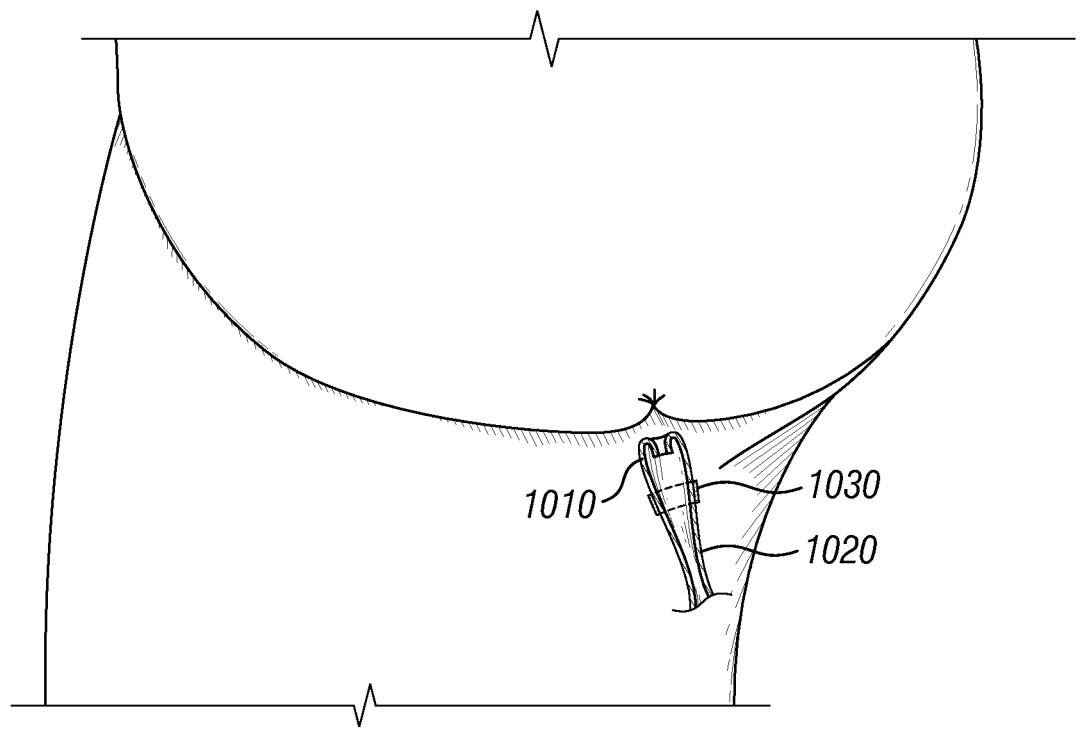
FIG. 10 shows an exemplary embodiment of the disclosed rectal collection device during installation.

Certain disclosed embodiments may be utilized for the collection of feces and/or other bodily fluids from the user's rectum and/or colon. As shown in the exemplary embodiments of FIG. 10, a single piece of tubular material may be folded over on itself in order to form a first sheath 1010 and second sheath 1020. A portion of the tubular material may be secured using an adhesive 1030, directly or indirectly, to the user such that the user's rectum and/or anus is substantially surrounded by the tubular material. In such embodiments, bodily fluid exiting the user may enter the first sheath 1010 and pass through the first opening in the first sheath 1010 into the volume defined by the second sheath 1020. In some embodiments, bodily fluid may then pass through the second opening in the second sheath 1020 and into a collection bag or other container.

Figure 11:
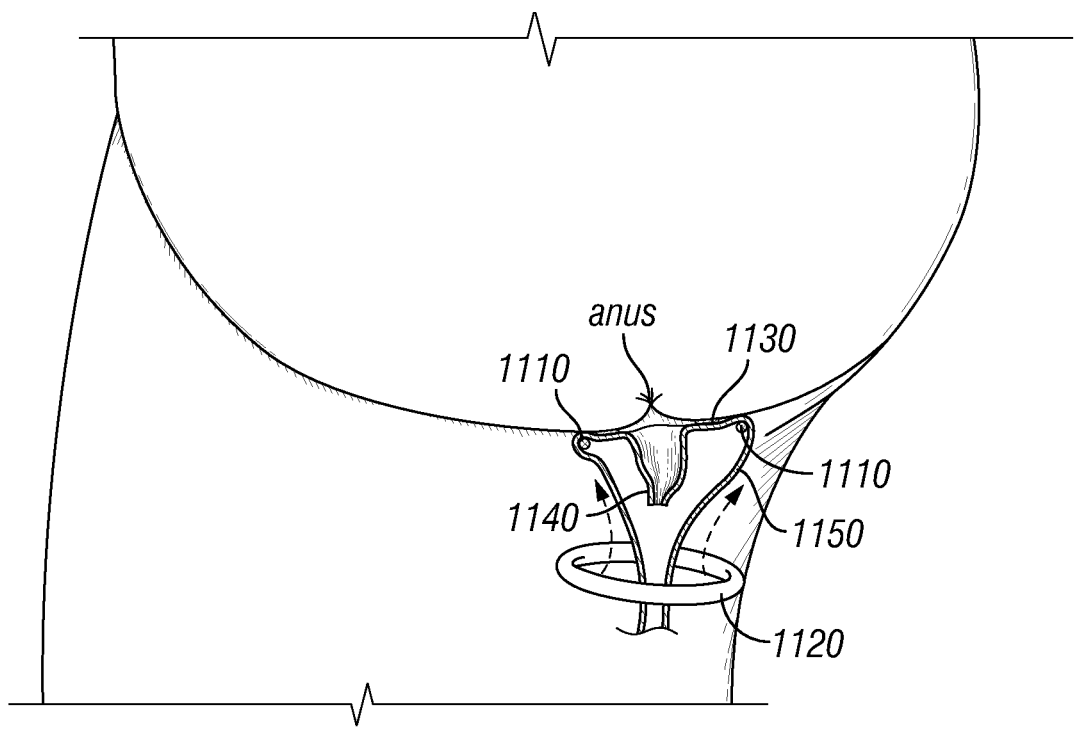
FIG. 11 shows one embodiment of the disclosed rectal collection device during installation.

As shown in FIG. 11, in some exemplary embodiments, a collection device may be secured to the user using a first retaining loop 1110 and second retaining loop 1120. The first retaining loop 1110 may be positioned outboard of the first sheath 1140 and inboard of the second sheath 1150. The second retaining loop 1120 may be positioned outboard of the second sheath 1150 and engage with the first retaining loop. In some embodiments, the inner diameter of the second retaining loop 1120 is smaller than the outer diameter of the first retaining loop 1110. In some embodiments, a hydrocolloid or other dressing may be secured to the user to reduce irritation to the user's skin. A gasket material 1130 may be additionally and/or alternatively be adhered or attached to the user and/or an intermediate layer and the collection device may be secured to the gasket material 1130. In such embodiments, bodily fluid or material may exit through the first sheath 1140 into the second sheath 1150. Utilizing the intermediate layers of a dressing and/or gasket material may facilitate forming a seal for containing any bodily fluids while simultaneously protecting the user's skin and facilitating replacement of the collection device as necessary.

Figure 12:
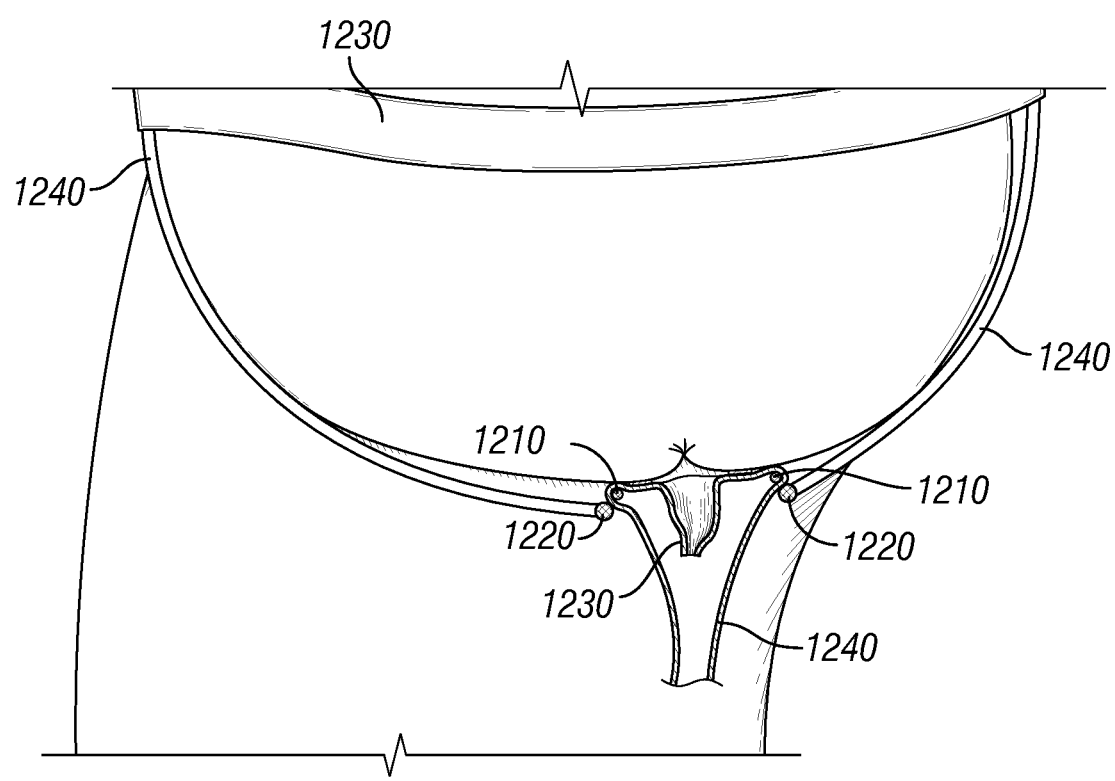
FIG. 12 shows an exemplary embodiment of the disclosed rectal collection device.

As shown in FIG. 12, in some exemplary embodiments, a collection device may be secured to the user using a first retaining loop 1210 and second retaining loop 1220. The second retaining loop 1220 may be configured to attach to a harness 1230 using a strap 1240. In some embodiments, the first retaining loop 1210 may be positioned outboard of the first sheath 1230 and inboard of the second sheath 1240. The second retaining loop 1220 may be positioned outboard of the second sheath 1240 and engage with the first retaining loop 1210 to secure the collection device to the user.

Some disclosed embodiments may be utilized to collect and/or isolate bodily fluid draining from wounds or other portions of the body. The drainage fluid may drain directly from a wound or may be from a surgical drain such as, for example, a Penrose drain.

Figure 13:
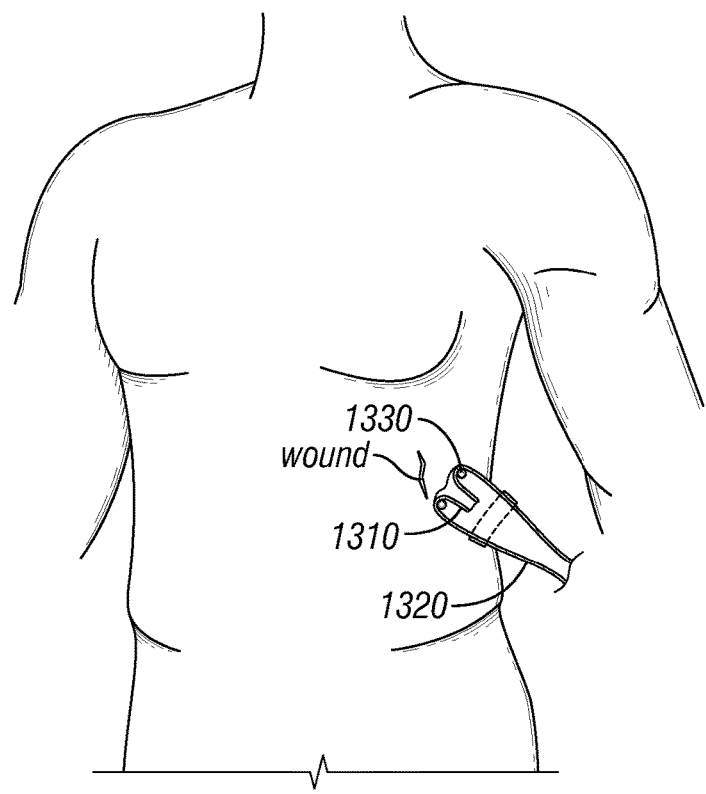
FIG. 13 shows an exemplary embodiment of the disclosed protection device during installation.

FIG. 13 shows an exemplary embodiment of a bodily fluid collection device with a first sheath 1310 which may be adhered or otherwise attached to the user around a wound or other penetration through the user's skin. The tubular material may be folded over the first retaining loop 1330 to form a first sheath 1310 and a second sheath 1320. In such embodiments, a wound, port, or surgical drain tube may be substantially surrounded by the first sheath 1310, thereby reducing or preventing contamination of the area.

Figure 14:
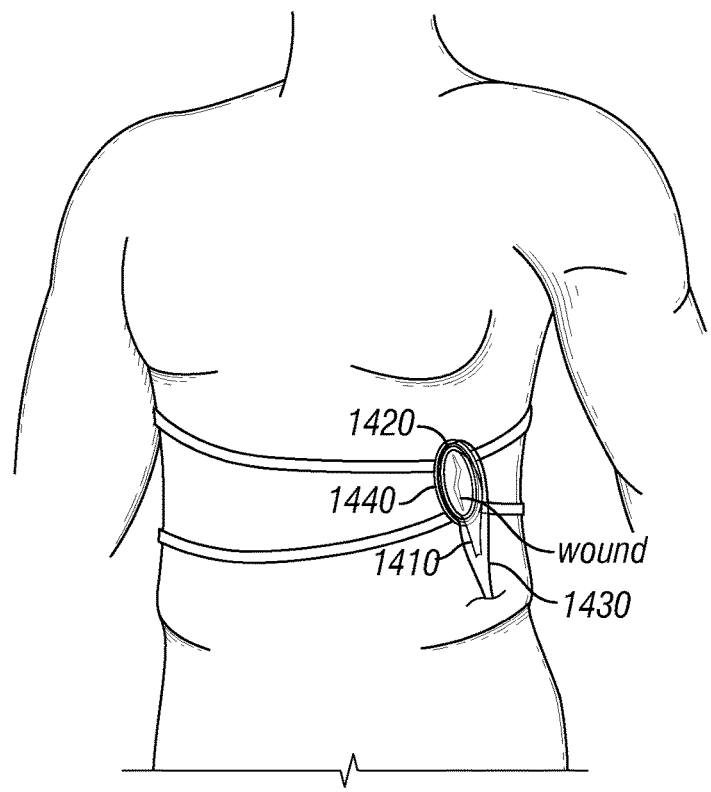
FIG. 14 shows one embodiment of the disclosed protection device during installation.

FIG. 14 shows an exemplary embodiment of a bodily fluid collection device being installed. As shown in FIG. 14, a portion of the first sheath 1410 of the tubular material may be adhered to the user's body, such that the first opening in the first sheath 1410 substantially surrounds a wound, port, or other penetration into the user's body. A first retaining loop 1420 may be positioned substantially surrounding the opening in the user's body, thereby retaining the first sheath 1410 which may be adhered to the user either directly or using an intermediate layer. The tubular material may be folded around the first retaining loop 1420 to form a second sheath 1430. A second retaining loop 1440 may be positioned outboard of the second sheath 1443 and positioned to engage the first retaining loop 1420 in a substantially similar manner as described in the context of other embodiments disclosed herein. It will be appreciated that the components, techniques, and features of any of the various embodiments disclosed herein may be applied to any other disclosed embodiment.

Figure 15:
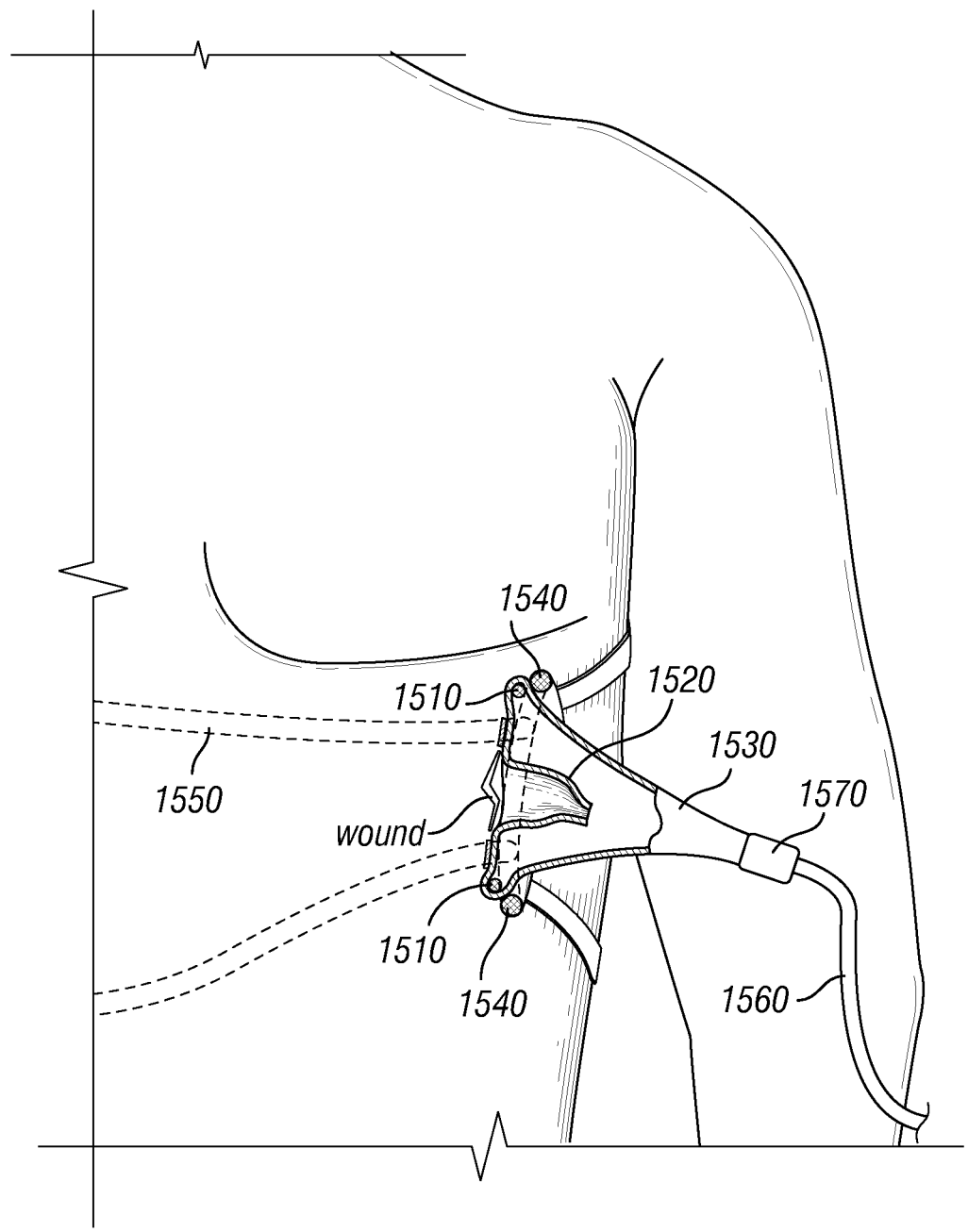
FIG. 15 shows an exemplary embodiment of the disclosed protection device.

FIG. 15 shows an exemplary embodiment of a bodily fluid collection device. As shown in FIG. 15, tubular material may be retained in position using a first retaining loop 1510 to form a first sheath 1520 and a second sheath 1530. A second retaining loop 1540 may be positioned outboard of the second sheath 1530 and may be secured to the user using a harness 1550. An ordinary artisan will appreciate that in order to retain the collection device in place, at least portions of the harness 1550 may be elastic in order to allow the user to breath and/or move while still retaining the collection device in position. As shown in FIG. 15, in some embodiments, the second sheath 1530 may be connected to a drain tube 1560 using a one-way valve 1570. Such embodiments allow bodily fluid to drain out of the first sheath 1520 and into a volume defined within the second sheath 1530. Then the fluid may drain through the one-way valve 1570 and into the drain tube 1560. In some embodiments, the drain tube 1560 may be connected to a fluid collection bag.

Figure 16:
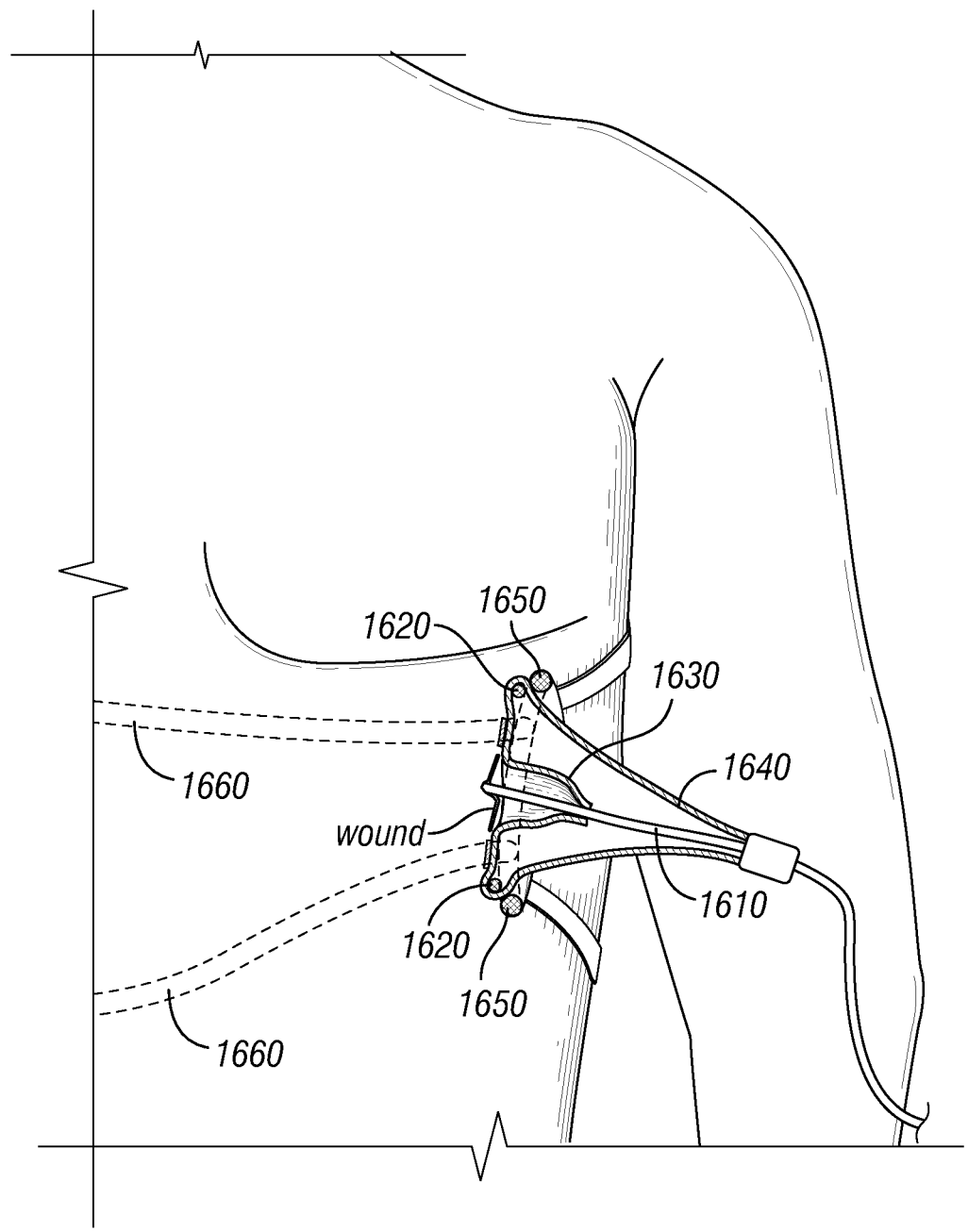
FIG. 16 shows an exemplary embodiment of the disclosed protection device.

FIG. 16 shows an exemplary embodiment of a bodily fluid collection device used with a surgical drain tube 1610. As shown in FIG. 16, the collection device may be retained in position using a first retaining loop 1620 to form a first sheath 1630 and a second sheath 1640. A second retaining loop 1650 may be positioned outboard of the second sheath 1640 and may be secured to the user using a harness 1660. As shown in FIG. 16, a drain tube from a surgically implanted drain 1610, such as, for example, a Penrose drain, may exit the user's body into the space on the interior of the first sheath 1630. The drain tube 1610 may then pass through the first opening in the first sheath 1620 and into the space defined within the second sheath 1640. In some embodiments, the opening of the second sheath 1640 may be configured to allow a drain tube 1610 to pass through. In some embodiments, the second sheath 1640 may be configured to be selectively attached to the drain tube 1610. This arrangement isolates the drainage site from the external environment, thereby reducing the risk of infection to the patient. It will be appreciated that, while this embodiment is described in terms of a Penrose drain tube for collection of bodily fluids from a wound, a similar embodiment may be utilized for protecting any drain tube exiting the user including, but not limited to the drain tube associated with a Foley catheter or other internal catheter or other internal drain.

Figure 17A:
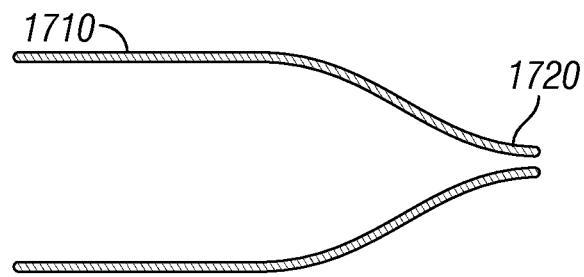
FIG. 17A shows a first sheath with a flutter valve according to an exemplary embodiment.

Exemplary embodiments disclosed herein may include a first and/or second sheath. In some embodiments, the first and or second sheath may be configured to include a flutter valve. FIG. 17A shows an embodiment of a sheath 1710 in which the tubular material is configured to form a flutter valve 1720. In some embodiments, a flutter valve may include a portion of tubular material which is allowed to passively closed. In some embodiments, the tubular material is shaped to have a reduced diameter at the openings. In some embodiments, the flutter valve may be a Heimlich valve. The flutter valve allows fluid to exit a sheath and inhibits any return flow of fluid which outside of the sheath.

Figure 17B:
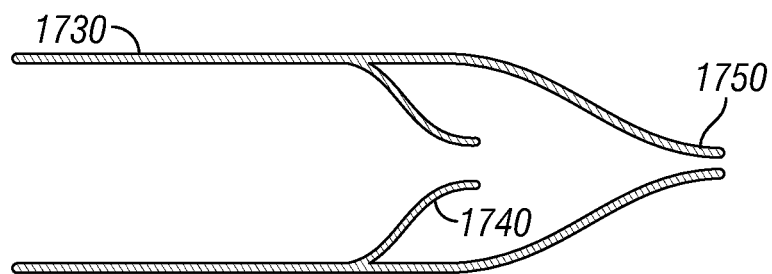
FIG. 17B shows a first sheath with a recessed flutter valve according to an exemplary embodiment.

FIG. 17B shows an exemplary embodiment of a sheath 1730 with a recessed flutter valve 1740 and a terminal flutter valve 1750. The recessed flutter valve 1740 may be formed substantially as described in the context of flutter valve 1720 in FIG. 17A, however, a recessed flutter valve 1740 does not generally define the end of a sheath. As shown in FIG. 17B, sheath 1730 continues past recessed flutter valve 1740 to terminal flutter valve 1750. The use of recessed flutter valve 1740 creates an additional one-way valve, thereby allowing fluid to be removed from a user. While FIG. 17B shows a single recessed flutter valve 1740, some embodiments may include multiple recessed flutter valves within a singles sheath. It will be appreciated that some embodiments utilizing flutter vales and/or recessed flutter vales may include material in addition to the single piece of tubular material used to form a first and second sheath.

Figure 17C:
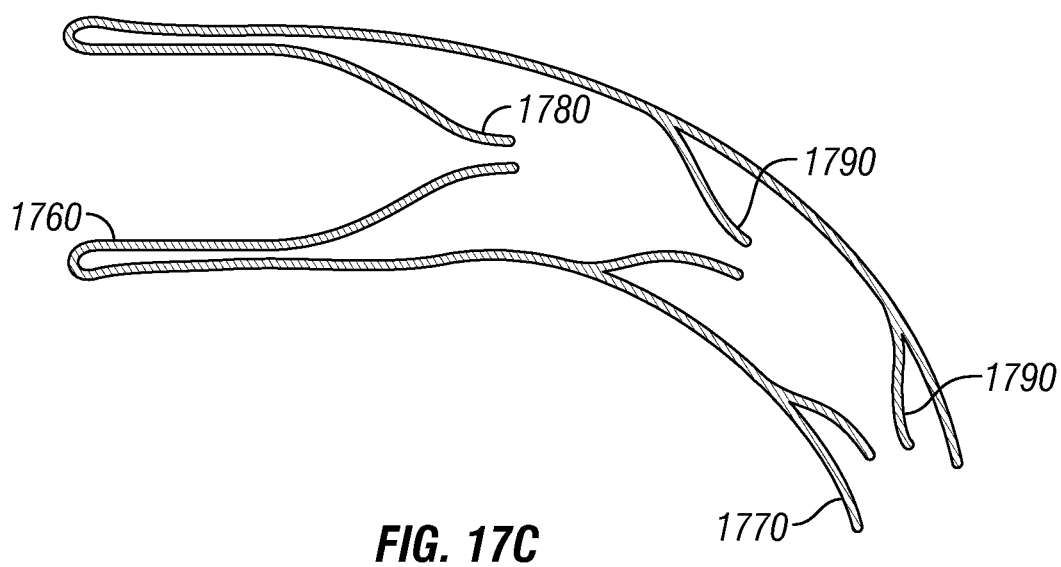
FIG. 17C shows an exemplary embodiment of the first sheath and second sheath with flutter vales.

FIG. 17C shows an exemplary embodiment of a fluid collection device with a first sheath 1760 and a second sheath 1770. First sheath 1760 terminates in a flutter valve 1780. Additionally, second sheath 1770 includes multiple recessed flutter valves 1790. It will be appreciated that each flutter valve substantially forms a one-way valve. Sheaths which include multiple flutter valves substantially form multiple compartments within the sheath. Each such compartment allows fluid to drain to the next compartment downstream and prevents fluid from flowing upstream towards the user. This arrangement allows for a passive system to drain fluid away from a user's body and prevent the fluid from subsequently contacting the user's body if the user rolls, moves, or is in a supine position. In some embodiments, a check valve may be used in addition to one or more than one flutter valves.

Figure 18:
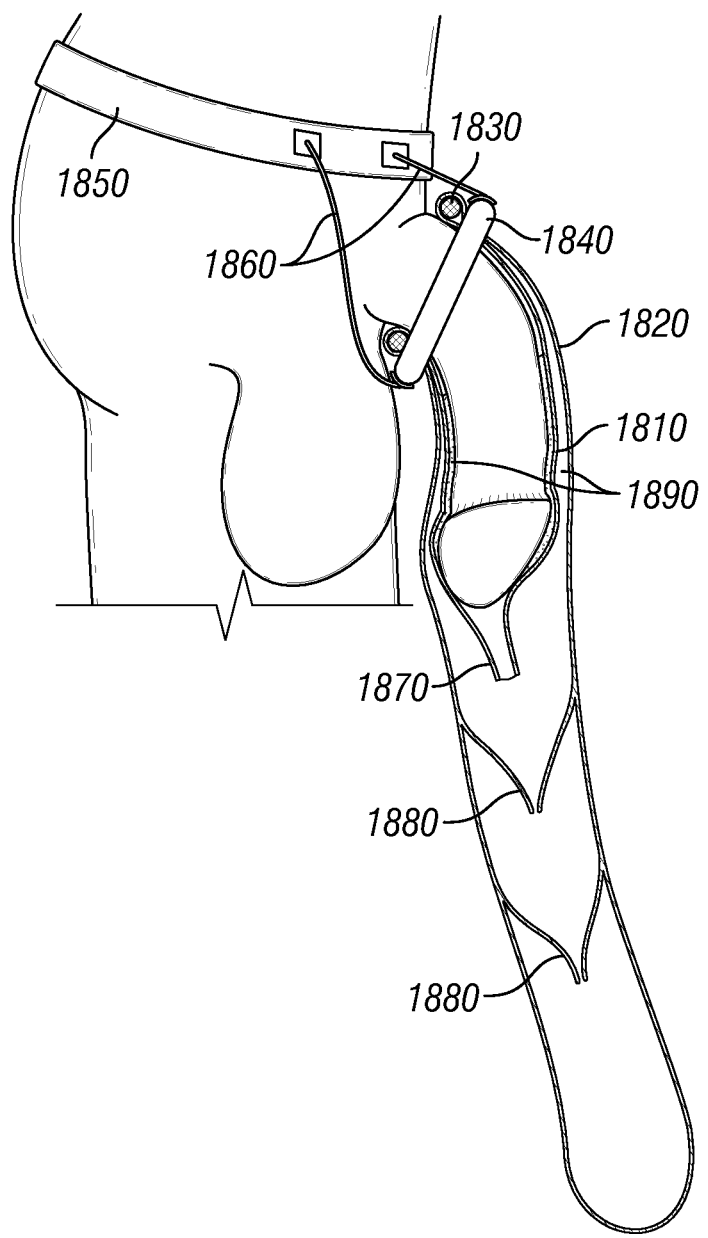
FIG. 18 depicts an exemplary embodiment with an extended second sheath.

FIG. 18 shows an embodiment of a male urine collection device including an extended second sheath. As shown in FIG. 18, the exemplary collection device includes a first sheath 1810 and an extended second sheath 1820 formed from a piece of tubular material. A first retaining loop 1830 is placed outboard of the first sheath 1810 and inboard of the second sheath 1820. A second retaining loop 1840 is positioned outboard of the second sheath 1820 and attached to a harness 1850 with a strap 1860. The first sheath 1810 terminates in a flutter valve 1870. The extended second sheath 1820 includes two recessed flutter valves 1880. Each of the recessed flutter valves 1880 creates an additional barrier inhibiting the return flow of a bodily fluid back to the user. In some embodiments, a jelly seal 1890 may be placed between the first sheath 1810 and second sheath 1820 or between the first sheath 1810 and the skin of the user's penis.

In some embodiments, the extended second sheath forms an integral fluid collection reservoir. Such embodiments may be used for applications which anticipate relatively low volumes of bodily fluid to be collected such as, for example, urine collection for an ambulatory user who may be incontinent. In some embodiments, the extended second sheath is sealed closed. In some embodiments, the extended second sheath may be open ended but be clamped or clipped closed in order to create a sealed fluid reservoir. In some embodiments, the second sheath is at least about 1 foot long, or at least about 2 feet long, or at least about 3 feet long. In some embodiments, the second sheath is at most about 1 foot long, or at most about 2 feet long, or at most about 3 feet long. In some embodiments, the second sheath is configured to extend along the leg of a user under his clothing and/or be attached to the body of a user. In some embodiments, the extended second sheath may contain absorbent material.

In the exemplary embodiment shown in FIG. 18, the extended second sheath is closed at the end. In some embodiments, the use of an extended second sheath allows the collection device to be used without a drain tube or fluid collection bag. It will be appreciated that such may require the fluid collection device to be removed once the extended second sheath is full. In some embodiments, the extended second sheath is configured to be fluidly connected to a drain tube and/or fluid collection bag, thereby allowing the fluid collection device to remain attached to the patient when the fluid collection bag is replaced.

Figure 19:
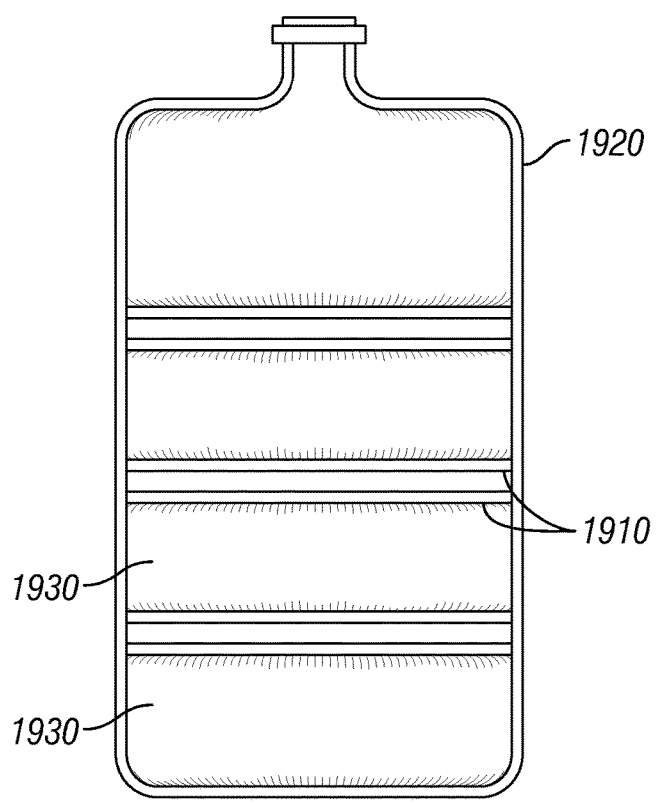
FIG. 19 depicts an exemplary embodiment of an extended fluid collection bag.

In some exemplary embodiments, the second opening of the second sheath will be configured to attach to a drain tube and/or collection bag. Typical collection bags include a single pouch which may be removed and replaced. FIG. 19 shows a collection bag with multiple tongue and groove seals 1910 within the body 1920 of the collection bag. These seals may be configured to form independently sealable pouches 1930. In some embodiments, multiple pairs of tongue and groove seals 1910 may be utilized to form independently removable pouches.

In some embodiments, two adjacent tongue and groove seals may be sealed shut to form a seal pouch. The lower seal of the adjacent pair of seals forms the sealed top of a lower pouch and the upper seal of the pair forms the sealed bottom of an upper pouch. Once both seals have been securely closed, the lower pouch may be removed from the collection bag by cutting the portion of the collection bag in between the two seals.

By removing a lower pouch from the remaining portion of the fluid collection bag, the weight associated with any collected bodily fluids may be reduced, thereby reducing the risk of a fluid collection device being dislodged. The removal of weight may also facility movement by the user. By allowing a portion of the collection bag to be removed, an extended collection bag may be used without being frequently replaced. This arrangement may save both material case and time associated with changing collection bags.

Figure 20:
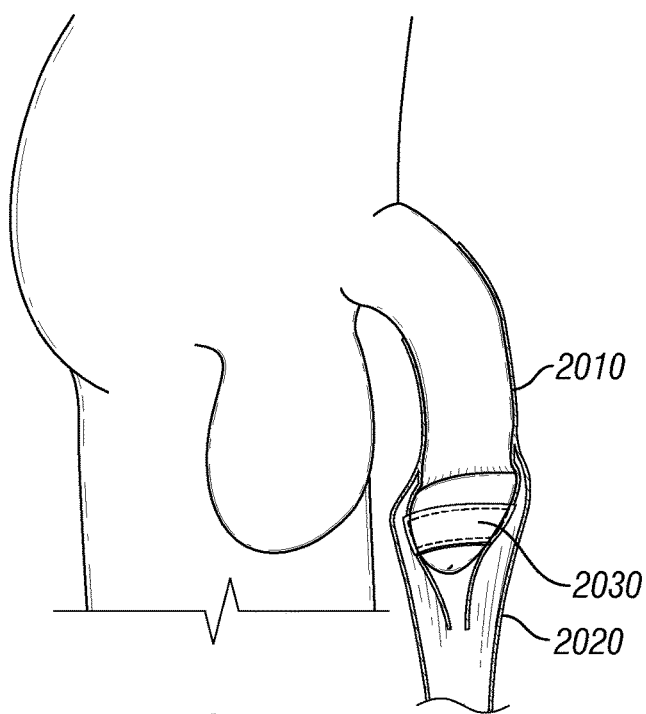
FIG. 20 depicts an exemplary embodiment of the disclosed device with an extended first sheath.

Some disclosed embodiments may be attached to the user without the use of retaining loops. FIG. 20 shows an exemplary embodiment of a male urine collection device including an extended first sheath 2010. As shown in FIG. 20, the extended first sheath may extend along the length of a user's penis. In some embodiments, the extended first sheath may include perforated or net-like material to provide air flow to the user's skin. In some embodiments, the increased surface area between the extended first sheath and the user's penis may result in sufficient forces necessary to retain the fluid collection device in place without the use of retaining loops. In some embodiments, the extended first sheath 2010 may be selectively secured to a user's penis using a separate material such as, for example, medical tape or an adhesive material 2030 such as, for example, a hydrocolloid dressing, Tegaderm, and/or Duoderm. In some embodiments, the first sheath 2010 is configured to not compress the user's penis.

As shown in the exemplary embodiment of FIG. 20, the second sheath 2020 may be attached to the first sheath. In some embodiments, the second sheath 2020 may be integral to the first sheath 2010. In some embodiments, the second sheath 2020 may include a separate piece of material which is connected to the first sheath 2010. In some embodiments, the second sheath 2020 is connected to the first sheath 2010 at a location configured to be behind the heat of the user's penis when the device is installed on a patient. In some embodiments, the second sheath 2020 folds around the head of the penis outboard of at least a portion of the first sheath 2010.

Some embodiments disclosed herein may be adhesively attached to the user to not rely on retaining loops. In some embodiments of a male urine collection device, the first end of the first sheath may be adhesively attached to the user's penis with or without an intermediate layer. In an exemplary embodiment, the first sheath may additionally be adhesively attached to the base of the user's penis. In some embodiments a breathable, porous, and/or non-irritating adhesive dressing, such as, for example, Hypafix tape, may be used to allow airflow to the user's skin. By adhesively attaching the first sheath to the user in two locations, the tubular material may fold over the adhesively attached first sheath to form a second sheath outboard of the first sheath. In such embodiments, the first sheath may be adhesively attached to the head of the user's penis or mid-shaft in addition to the base of the user's penis. It will be appreciated that embodiments which are adhered to the mid-shaft of a user's penis may be useful for ambulatory users as urine will naturally flow down and away from the user's skin while the user is sitting or standing as opposed to supine.

Figure 21:
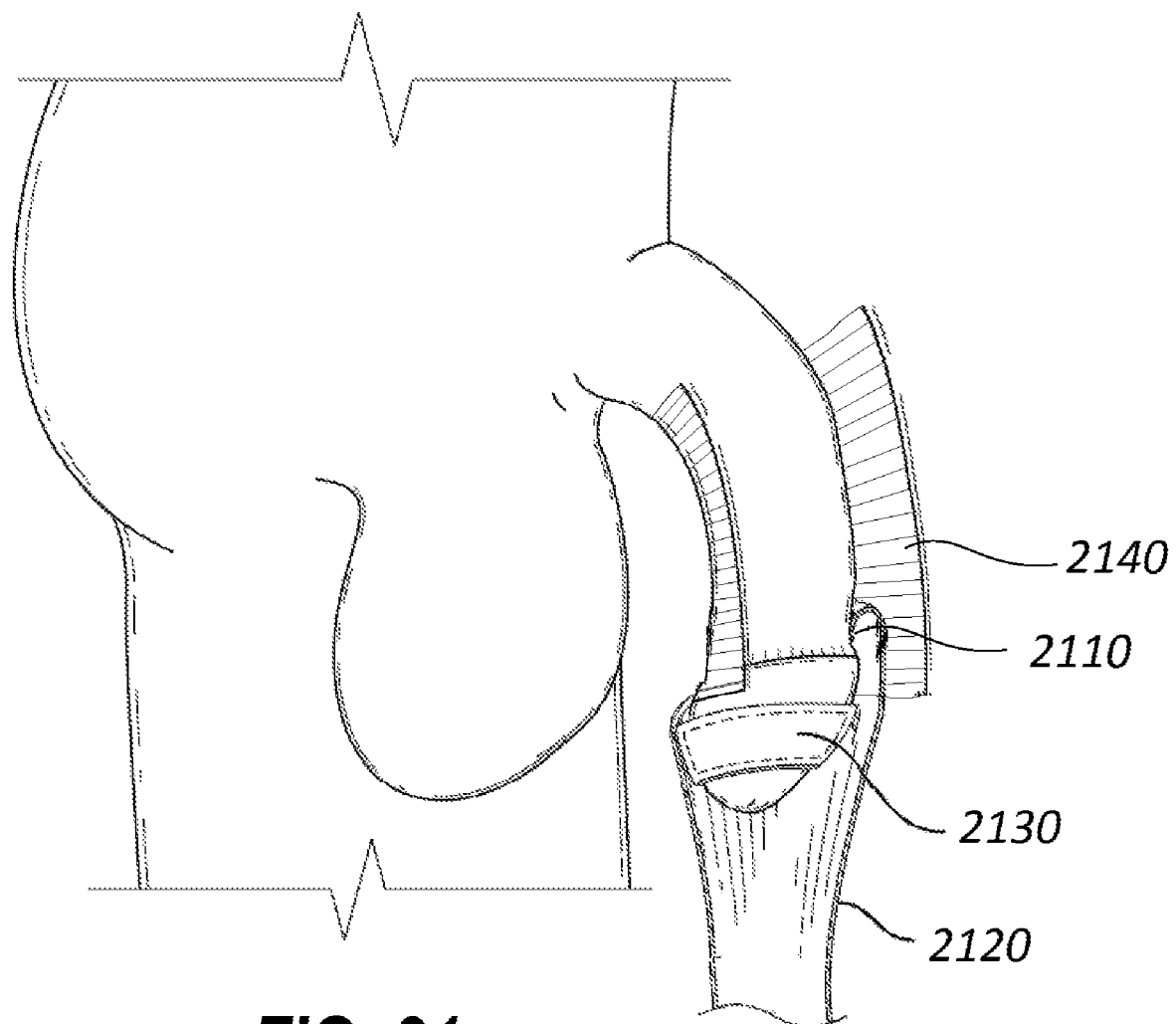
FIG. 21 depicts an exemplary embodiment of the disclosed device with an adhesive attachment.

In some embodiments, a male urine collection device may be adhesively secured to the user without the use of retaining loops or an extended first sheath. As shown in FIG. 21 a male collection comprising a first sheath 2110 and a second sheath 2120 may be initially applied to a user as described above with the second sheath 2120 being folded outboard of the first sheath 2110. In some embodiments, the first sheath 2110 may be adhesively attached to the glans of the penis using an intermediate layer 2130. A porous tape 2140, such as, for example, Hypafix tape, may be used to secure the male urine collection device to the shaft of the penis. As shown in FIG. 21, a piece of tape 2140 may be applied to the exterior of the second sheath 2120 covering the portion of the collection device at which the tubular material is folded over to form the first and second sheaths. The tape 2140 may also be applied to at least a portion of the shaft of the penis, thereby adhesively securing the collection device to the user without the use of retaining loops. It will be appreciated that the tape 2140 may be applied in such as manner to avoid compression of the penis or substantial compression of the penis.

Some embodiments disclosed herein may comprise one or more inflatable portions. These inflatable portions may be configured to allow portions of the fluid collection device to float if urine or another liquid pools without draining from the device. In some embodiments, the floating portions prevent a user's body from being or remaining in contact with a pooled liquid. In some embodiments, the inflatable portion may be inflated using a syringe or a source of pressurized air. In some embodiments, the inflatable portion may be configured as a single or multiple straight or curved lines, a half moon or a semi-circular pocket. In male urine collection embodiments, inflatable portions should not create undue pressure around the penis when inflated.

In some embodiments, a hydrophobic coating may be applied to the interior and/or exterior of the tubular material and/or other components of the fluid collection device. In some embodiments, the material used to form the device, either partially or entirely, may be hydrophobic by nature. Such materials may facilitate the flow and/or removal of bodily fluids away from a user.

In some embodiments, a desiccant or highly absorbent material may be contained within the device. In some embodiments, a desiccant and/or highly absorbent material may be placed within a fluid collection bag or other container to prevent movement of any captured fluid. In some embodiments, a desiccant and/or highly absorbent material may be used to prevent or minimize contact between a user's skin and any bodily fluid.

Some embodiments include an antibacterial, antifungal, and/or antimicrobial coating and/or material. In some embodiments, a jelly seal may contain antibiotics, antifungal, and/or antimicrobial agents.

Some embodiments may comprise a reservoir and access port which may be used to access a sample of the collected bodily fluid. Bodily fluid, such as, for example, urine, may be used for performing a wide variety of diagnostic tests. Such tests include, but are not limited to pregnancy tests, pH, urine glucose, urine protein, urine chemistry, and/or bacterial culturing. In some embodiments, the access port may be formed by, for example, a tongue and groove seal, or a portion of the material that is designed to be pierced with a hypodermic needle.

In some disclosed embodiments the device is attached to the user using a single retaining loop with magnetic attachment. In such embodiments, the first retaining loop may be magnetized, may have magnetic components, or may include metal components and secured to a magnetic component attached to the user. In some embodiments, the use of magnetic attachment to secure the first retaining loop eliminates the need for a second retaining loop. It will be appreciated that a component of a base or harness attached to the user and/or a component of the retaining loop may be magnetized in order to secure a fluid collecting device to the user. It is not required that both a component of the base and a retaining loop are magnetized.

Disclosed embodiments may relate to a fluid collection device comprising a tubular member comprising a first end with a first opening and a second end with a second opening, a portion of the first end configured to be adhesively secured to a user and the second end configured to fold around the first end forming a first sheath and a second sheath wherein the second sheath is outboard of the first sheath and defines an interior volume; a first retaining loop having an inner diameter and an outer diameter, the first retaining loop configured to be positioned outboard of the first sheath and inboard of the second sheath; and a second retaining loop having an inner diameter and an outer diameter, the inner diameter of the second retaining loop being less than the outer diameter of the first retaining loop. In some embodiments, the second sheath is configured to attach to a fluid collection bag and/or the second retaining loop is configured to attach to a harness. Some embodiments, further comprise a harness and a strap, the harness configured to be positioned around a user and the strap configured to connect the second retaining loop to the harness. In some embodiments, the strap comprises an elastic material; the first sheath is configured to extend beyond the glans of the penis and allow a drain tube to pass through the first opening; the drain tube is configured to drain fluid into the interior volume defined by the second sheath; the first sheath comprises a flutter valve; the first sheath comprises a recessed flutter valve; and/or the second sheath comprises at least one flutter valve. Some embodiments further comprise a one-way valve connecting the second sheath to a drain tube and wherein the drain tube is connected to a fluid collection bag; a fluid collection bag comprising multiple tongue and groove seals; and/or an adhesive layer positioned at the first end of the tubular member. In some embodiments, the first retaining loop is configured to be positioned around a penis and avoid compression of the penis.

Disclosed embodiments may relate to a male urine collection device comprising a tubular member with a first end and a second end; the tubular member configured to fold over on itself to form a first sheath and a second sheath, wherein the first sheath is configured to be positioned around a penis and the second sheath is outboard of the first sheath; wherein the second sheath defines an interior volume and is configured to in fluid communication with a fluid collection bag; and a first retaining loop with an inner diameter and an outer diameter, the first retaining loop configured to be positioned around the penis outboard of the first sheath and inboard of the second sheath, the first retaining loop configured to avoid compression of the penis. In some embodiments, a first opening in the first sheath is configured to allow an indwelling catheter drain tube to pass through the first opening and wherein an second opening in the second sheath is configured to be secured around the drain tube. Some embodiments further comprise a second retaining loop having an inner diameter and an outer diameter, the outer diameter of the first retaining loop being greater than the inner diameter of the second retaining loop, and the second retaining loop configured to be attached to a harness by a strap.

Disclosed embodiments may relate to a ale urine collection device comprising a first sheath with a first end comprising a first opening and a second end comprising a second opening, the first opening configured to allow the penis to be inserted into the first end of the first sheath, the second end configured to extend past the glans of the penis, and the second opening comprising a flutter valve; and a second sheath attached to the exterior of the first sheath, the second sheath outboard of the second end of the first sheath and defining an interior volume. In some embodiments, the first end of the first sheath comprises multiple vent openings to allow airflow to a portion of the penis and/or the second end of the first comprises an adhesive layer.

Throughout the specification and the claims, the following terms take at least the meanings explicitly associated herein, unless the context clearly dictates otherwise. The term "or" is intended to mean an inclusive "or." Further, the terms "a," "an," and "the" are intended to mean one or more unless specified otherwise or clear from the context to be directed to a singular form. The term "tubular" is intended to cover round, rectangular, irregular, or any other cross-sectional geometries so long as they component is hollow. The term "tubular" is not limited to round or circular cross sections and includes many variations. The term "diameter" is intended to cover the distance from one side of a shape to the other and is intended to cover any cross-sectional shape. The term "diameter" is not limited to circular or round shapes but includes rectangular, angled, and irregular shapes as well.

In this description, numerous specific details have been set forth. It is to be understood, however, that implementations of the disclosed technology may be practiced without these specific details. In other instances, well-known methods, structures and techniques have not been shown in detail in order not to obscure an understanding of this description. References to "some examples," "other examples," "one example," "an example," "various examples," "one embodiment," "an embodiment," "some embodiments," "example embodiment," "various embodiments," "one implementation," "an implementation," "example implementation," "various implementations," "some implementations," etc., indicate that the implementation(s) of the disclosed technology so described may include a particular feature, structure, or characteristic, but not every implementation necessarily includes the particular feature, structure, or characteristic. Further, repeated use of the phrases "in one example," "in one embodiment," or "in one implementation" does not necessarily refer to the same example, embodiment, or implementation, although it may.

While certain implementations of the disclosed technology have been described in connection with what is presently considered to be the most practical and various implementations, it is to be understood that the disclosed technology is not to be limited to the disclosed implementations, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain implementations of the disclosed technology, including the best mode, and also to enable any person skilled in the art to practice certain implementations of the disclosed technology, including making and using any devices or systems and performing any incorporated methods. The patentable scope of certain implementations of the disclosed technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A fluid collection device comprising: a tubular member comprising a first end with a first opening and a second end with a second opening, a portion of the first end configured to be adhesively secured to a user and the second end configured to fold around the first end forming a first sheath and a second sheath wherein the second sheath is outboard of the first sheath and defines an interior volume; a first retaining loop having an inner diameter and an outer diameter, the first retaining loop configured to be positioned outboard of the first sheath and inboard of the second sheath; and a second retaining loop having an inner diameter and an outer diameter, the inner diameter of the second retaining loop being less than the outer diameter of the first retaining loop, wherein the first sheath is secured to the user using a separate material or an adhesive material; the second retaining loop is slid over the second sheath and engages with the first retaining loop; and wherein the second retaining loop is configured to attach to a harness.

2. The fluid collection device of claim 1, wherein the second sheath is configured to attach to a fluid collection bag.

3. The fluid collection device of claim 1, further comprising a harness and a strap, the harness configured to be positioned around a user and the strap configured to connect the second retaining loop to the harness.

4. The fluid collection device of claim 3, wherein the strap is elastic.

5. The fluid collection device of claim 1, wherein the first sheath is configured to extend beyond the glans of the penis and allow a drain tube to pass through the first opening.

6. The fluid collection device of claim 5, wherein the drain tube is configured to drain fluid into the interior volume defined by the second sheath.

7. The fluid collection device of claim 1, wherein the first sheath comprises a flutter valve.

8. The fluid collection device of claim 1, wherein the first sheath comprises a recessed flutter valve.

9. The fluid collection device of claim 1, wherein the second sheath comprises at least one flutter valve.

10. The fluid collection device of claim 1, further comprising a one-way valve connecting the second sheath to a drain tube and wherein the drain tube is connected to a fluid collection bag.

11. The fluid collection device of claim 1, further comprising a fluid collection bag comprising tongue and groove seals.

12. The fluid collection device of claim 1, wherein the first retaining loop is configured to be affixed around a penis and avoid substantial compression of the penis.

13. The fluid collection device of claim 1, further comprising an adhesive layer positioned at the first end of the tubular member.

14. A male urine collection device comprising: a tubular member with a first end and a second end; the tubular member configured to fold over on itself to form a first sheath and a second sheath, a first retaining loop with an inner diameter and an outer diameter, and a second retaining loop is slid over the second sheath and engages with the first retaining loop, wherein the first sheath is configured to be positioned around a penis and the second sheath is outboard of the first sheath, and the first sheath is secured to the user using a separate material or an adhesive material; wherein the second sheath defines an interior volume and is configured to in fluid communication with a fluid collection bag; the first retaining loop configured to be positioned around the penis outboard of the first sheath and inboard of the second sheath, the first retaining loop configured to avoid compression of the penis; and wherein the second retaining loop is configured to attach to a harness.

15. The male urine collection device of claim 14, wherein a first opening in the first sheath is configured to allow an indwelling catheter drain tube to pass through the first opening and wherein a second opening in the second sheath is configured to be secured around the drain tube.

16. The male urine collection device of claim 14, wherein the second retaining loop has an inner diameter and an outer diameter, the outer diameter of the first retaining loop being greater than the inner diameter of the second retaining loop, and the second retaining loop configured to be attached to a harness by a strap.

17. A male urine collection device comprising: a first sheath with a first end comprising a first opening and a second end comprising a second opening, the first opening configured to allow the penis to be inserted into the first end of the first sheath, the second end configured to extend past the glans of the penis, and the second opening comprising a flutter valve; and a second sheath attached to the exterior of the first sheath, the second sheath outboard of the second end of the first sheath and defining an interior volume wherein the first sheath is secured to the user using a separate material or an adhesive material; a second retaining loop is slid over the second sheath and engages with a first retaining loop; and wherein the second retaining loop is configured to attach to a harness.

18. The male urine collection device of claim 17, wherein the first end of the first sheath comprises one or more vent openings to allow airflow to a portion of the penis.

19. The male urine collect on device of claim 17, wherein the second end of the first comprises an adhesive layer.

* * * * *